(12) United States Patent
Sharma et al.

(10) Patent No.: US 10,135,459 B2
(45) Date of Patent: Nov. 20, 2018

(54) ADC WITH CAPACITIVE DIFFERENCE CIRCUIT AND DIGITAL SIGMA-DELTA FEEDBACK

(71) Applicants: Yogesh Jayaraman Sharma, Santa Clara, CA (US); Arthur J. Kalb, Santa Clara, CA (US)

(72) Inventors: Yogesh Jayaraman Sharma, Santa Clara, CA (US); Arthur J. Kalb, Santa Clara, CA (US)

(73) Assignee: Analog Devices, Inc., Norwood, MA (US)

( * ) Notice: Subject to any disclaimer, the term of this patent is extended or adjusted under 35 U.S.C. 154(b) by 0 days.

(21) Appl. No.: 15/334,011

(22) Filed: Oct. 25, 2016

(65) Prior Publication Data

US 2018/0115320 A1    Apr. 26, 2018

(51) Int. Cl.
  *H03M 3/00*   (2006.01)
  *A61B 5/0428*  (2006.01)
  *A61B 5/00*   (2006.01)

(52) U.S. Cl.
  CPC ......... *H03M 3/464* (2013.01); *A61B 5/04284* (2013.01); *A61B 5/7203* (2013.01); *H03M 3/422* (2013.01); *H03M 3/496* (2013.01)

(58) Field of Classification Search
  CPC ....... H03M 3/464; H03M 3/422; H03M 3/496
  USPC ................. 341/143, 155, 144, 172
  See application file for complete search history.

(56) References Cited

U.S. PATENT DOCUMENTS

| | | |
|---|---|---|
| 5,327,133 A | 7/1994 | Greene |
| 5,635,864 A | 6/1997 | Jones |
| 6,271,782 B1 | 8/2001 | Steensgaard-Madsen |
| 7,095,345 B2 | 8/2006 | Nguyen et al. |
| 7,385,443 B1 | 6/2008 | Denison |
| 7,423,567 B2 * | 9/2008 | Melanson ............. H03M 3/412 341/143 |
| 8,094,051 B2 | 1/2012 | Bos |
| 8,265,769 B2 | 9/2012 | Denison |
| 9,391,628 B1 | 7/2016 | Lyden et al. |
| 9,419,642 B1 | 8/2016 | Nguyen |
| 9,588,497 B1 | 3/2017 | Monk et al. |
| 2007/0126615 A1 | 6/2007 | Kim et al. |
| 2009/0085785 A1 | 4/2009 | Gerfers et al. |
| 2010/0066577 A1 * | 3/2010 | Huang .................. H03F 1/0277 341/143 |

(Continued)

OTHER PUBLICATIONS

"Optimum Selection of Capacitive Array for Multibit Sigma-Delta Modulators without DEM", (Jan. 1, 2009), 4 pgs.

(Continued)

*Primary Examiner* — Peguy Jean Pierre
(74) *Attorney, Agent, or Firm* — Schwegman Lundberg & Woessner, P.A.

(57) ABSTRACT

A low power high precision mixed signal analog to digital converter is provided for processing biometric signals in the presence of a large interferer signal for cableless patient monitoring; a capacitive difference circuit produces an analog difference signal by differencing an analog feedback loop signal and an input signal; an analog-to-digital converter sigma delta converter produces a digital version of the difference signal, a digital feedback loop includes a digital integrator and a capacitive digital-to-analog converter configured to produce the analog loop feedback signal based upon the digital version of the difference.

20 Claims, 7 Drawing Sheets

(56) References Cited

U.S. PATENT DOCUMENTS

| | | | |
|---|---|---|---|
| 2010/0075624 A1* | 3/2010 | Shanan | H04L 25/06 |
| | | | 455/253.2 |
| 2012/0038500 A1* | 2/2012 | Dijkmans | H03M 3/434 |
| | | | 341/143 |
| 2012/0154193 A1 | 6/2012 | Chang et al. | |
| 2012/0281786 A1 | 11/2012 | Lindemann et al. | |
| 2015/0145571 A1 | 5/2015 | Perrott | |
| 2015/0256194 A1* | 9/2015 | Saito | H03M 3/46 |
| | | | 341/156 |
| 2018/0132750 A1 | 5/2018 | Kalb et al. | |
| 2018/0138920 A1 | 5/2018 | Sharma et al. | |

OTHER PUBLICATIONS

Bohorquez, Jose L., et al., "A Digitally-Assisted Sensor Interface for Biomedical Applications", 2010 Symposium on VLS! Circuits/Technical Digest of Technical Papers, (2010), 217-218.

Bryant, Michael D., et al., "A Mixed Signal (Analog-Digital) Integrator Design", IEEE Transactions on Circuits and Systems-1: Regular Papers, 59)7), (Jul. 2012), 14-9.

Denison, Tim, et al., "A 2uW 100 n V/rtHz Chopper-Stabilized Instrumentation Amplifier for Chronic Measurement of Neutral Field Potentials", IEEE Journal of Solid-State Circuits, vol. 42, No. 12, (Dec. 2007), 2934-2945.

Muller, Rikky, et al., "A 0.13 mm2, 5uW, DC-Coupled Neutral Signal Acquisition IC With 0.5 V Supply", IEEE Journal of Solid-State Circuits, vol. 47, No. 1, (Jan. 2012), 232-243.

"U.S. Appl. No. 15/621,621, Preliminary Amendment filed Nov. 3, 2017", 6 pgs.

\* cited by examiner

FIG. 7

ADC WITH CAPACITIVE DIFFERENCE CIRCUIT AND DIGITAL SIGMA-DELTA FEEDBACK

BACKGROUND OF THE INVENTION

Biometric signals are electronic signals indicative of a patient's physiological condition such as blood pressure, respiration and heartbeat. Modern hospital patient monitoring systems are moving toward a cable-less environment in which a patient wears one or more devices that transmit biometric data signals wirelessly to a data processing system located nearby to the patient. A patient wears one or more batter powered sensor devices that transmit data wirelessly to an aggregator such as a nurse's station. These wearable devices allow hospital staff to remotely monitor patient vital signs. Such a wireless system results in fewer cases of infections, better safety by less cabling in workplace, less redundant work for cabling, less annoyance for the patient, improved patient mobility, for example.

SUMMARY

A low power high precision mixed signal analog-to-digital converter system is provided for processing biometric signals in the presence of a large interferer signal for cableless patient monitoring.

In one aspect, analog-to-digital converter system includes a capacitive difference circuit that produces an analog difference signal by differencing an analog feedback loop signal and an input signal. A sigma delta converter produces a digital version of the difference signal. A digital feedback loop includes a digital integrator and a capacitive digital-to-analog converter that is configured to produce the analog loop feedback signal based upon the digital version of the difference signal.

In another aspect, an analog-to-digital converter system includes a capacitive difference circuit that is coupled to receive an analog input signal and to receive an analog feedback signal and to provide an analog difference signal representing their difference. A capacitive amplifier circuit is setup to receive the analog difference signal and to provide an amplified analog difference signal. A sigma-delta analog-to-digital converter is coupled to produce a digital output signal based upon the amplified analog difference signal. A digital integrator circuit is coupled to receive the digital output signal and to provide a digital integration signal. A capacitive digital-to-analog converter (DAC) is coupled to produce the analog loop feedback signal based upon the digital integration signal.

DESCRIPTION OF EMBODIMENTS

A signal of interest often is received together with multiple interferer signals. An analog to digital converter (ADC) with a mixed signal sigma-delta feedback loop removes the dominant interferer signal in the course of converting a signal of interest, such as a biometric signal, from analog to digital domain. The converter receives as input the signal of interest and the interferer. The circuit produces a feedback signal to cancel the interferer. A capacitive difference circuit receives the input signal and the feedback signal and provides the signal of interest with the interferer removed in one embodiment. The use of capacitance DAC and amplifier to remove the interferer results in achieving high precision signal processing.

An electrocardiograph (ECG) signal is a biometric signal indicative of heart activity. Electrocardiography is the process of recording the electrical activity of the heart over a period of time using electrodes placed on the skin. These electrodes detect the tiny electrical changes on the skin that arise from the heart muscle's electrophysiologic pattern of depolarizing during each heartbeat. The overall magnitude of the heart electrical potential is measured from multiple different angles using leads placed at different locations on the human body and is recorded over a period of time (typically 10 seconds). To a trained clinician, an ECG conveys a large amount of information about not only the structure of the heart but also the function of its electrical conduction system.

Figure 1:
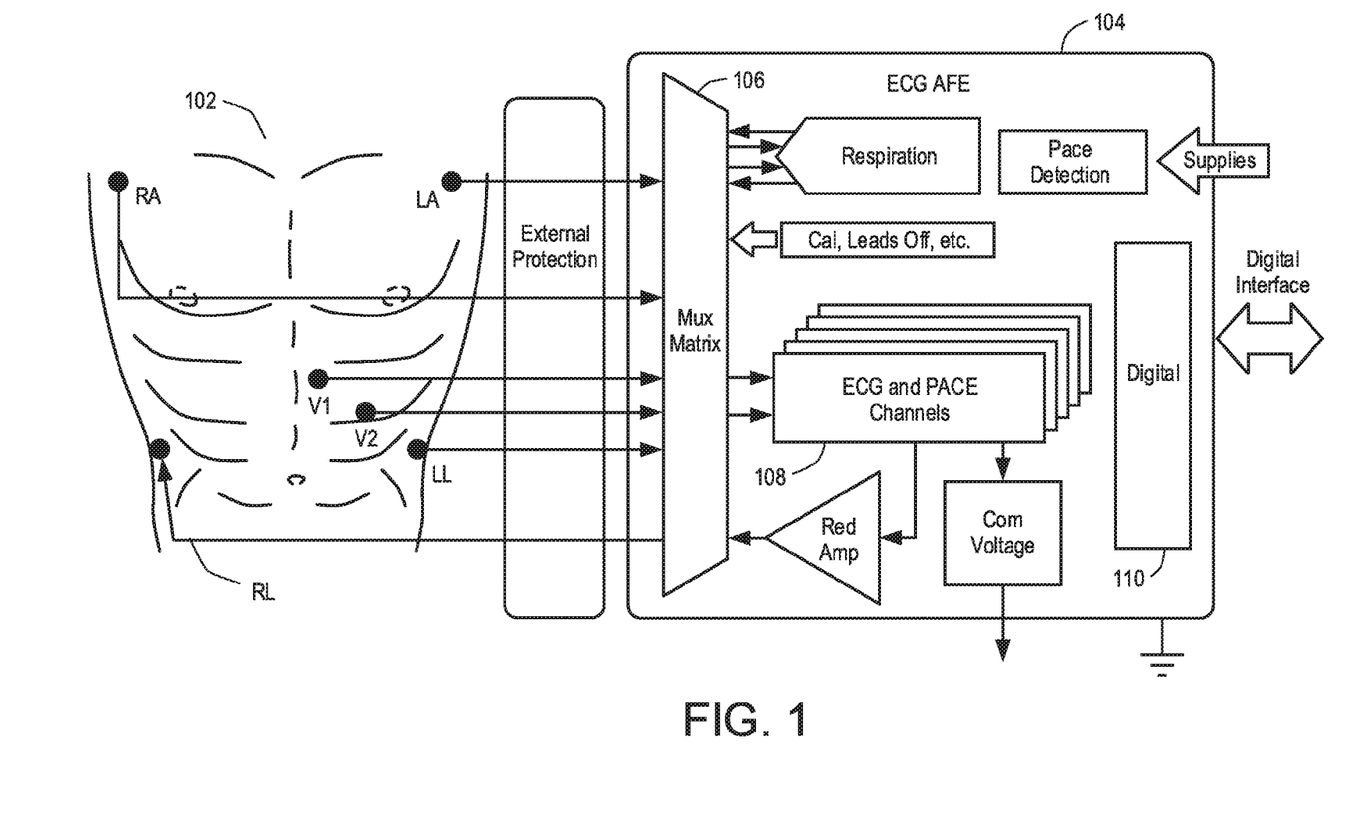
FIG. 1 is an illustrative drawing showing electrical ECG leads in contact with patient's abdomen and a functional block diagram of a biometric monitoring analog front end (AFE) coupled to monitor biometric signals received on the leads.

FIG. 1 is an illustrative drawing showing electrical ECG leads in contact with patient's abdomen 102 and a functional block diagram of a biometric monitoring analog front end (AFE) 104 coupled to monitor biometric signals received on the leads. In accordance with some embodiments, the biometric monitoring system 104 monitors ECG signals. Input leads RA, LA, V1, V2 and LL are used to sense individual ECG signals at different locations on the abdomen 102, which are used to produce multiple differential channel signals. In some embodiments, the differential channel signals include, channel 1=LA-RA, channel 2=LL-RA, channel 3=LA-LL, channel 4=V1-RA and channel 5=V2-RA. An RL lead is used to force a common mode voltage close to a reference level to achieve maximum input dynamic range. The monitoring system 104 includes multiplexing circuitry 106 that couples each lead to respective converter circuits, 108 that convert the analog ECG signals to corresponding digital ECG versions of the signals. The monitoring system includes digital interface circuitry 110 to transmit the digital ECG signals to processing circuitry (not shown).

Figure 2:
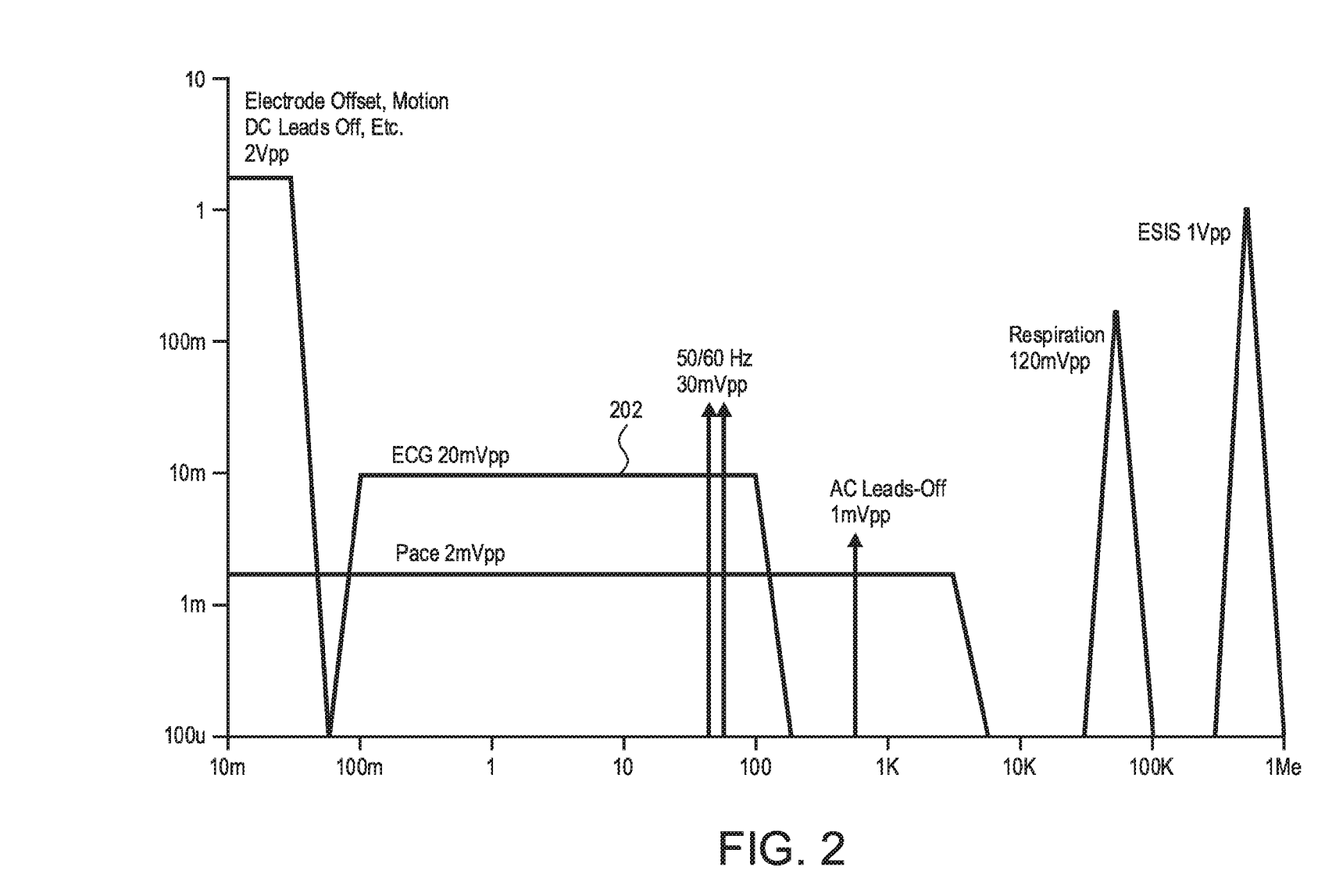
FIG. 2 is an illustrative voltage versus frequency diagram in which a y axis represents example voltages of an ECG signal and multiple example interferer signals and an x axis represents a signal frequency range in accordance with some embodiments.

FIG. 2 is an illustrative voltage versus frequency diagram in which a y axis represents example voltages of an ECG signal 202 and multiple example interferer signals and an x axis represents a signal frequency range. A typical ECG signal has a maximum amplitude of +/−10 mV with a frequency content between 50 mHz and 150 Hz. The example ECG has an amplitude of 20 mVpp. The electrode-skin interface is affected by numerous interferers due to bio-distortion arising from contact potential and contact impedance. Polarization of the electrode-skin interface can develop a half-cell potential for wet Ag/AgCl electrode of about +/−300 mV that can drift slowly due to motion artifacts. Mismatch in contact and filter impedance can convert common mode interferers such as a 50/60 Hz line frequency into a differential interferer. Implanted pacemakers can generate brief rectangular pulses with amplitudes up to about 700 mV while the stimulus for some respiration sensing can be as large as about 2Vpp at the electrode. The ECG monitoring system 104 may be operated during electro-surgery (ESIS) involving application of high-frequency alternating polarity (e.g., 200V, 2 MHz) electrical drive used to cut and coagulate tissue.

Figure 3:
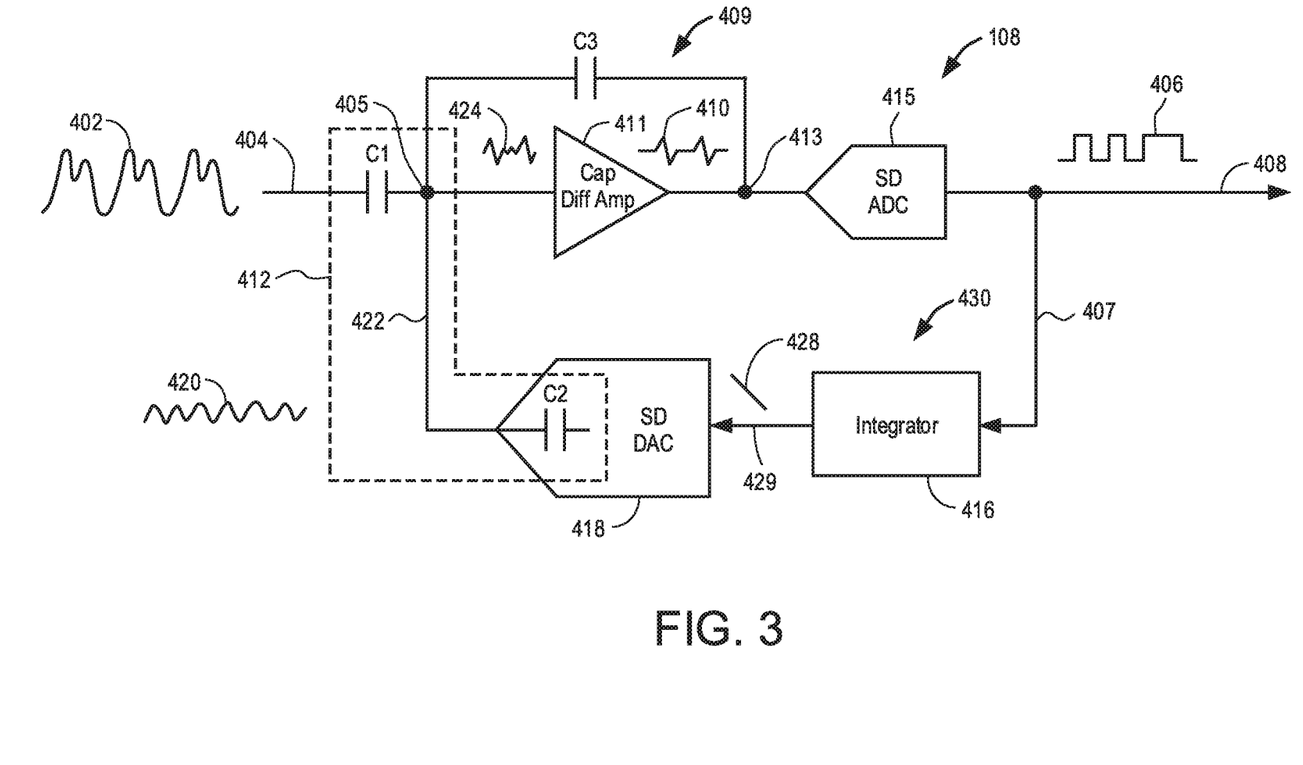
FIG. 3 is an illustrative circuit diagram representing an individual converter circuit of the biometric monitoring system of FIG. 1 in accordance with some embodiments.

FIG. 3 is an illustrative circuit diagram representing an individual analog to digital converter circuit 108 of the biometric monitoring system 104 of FIG. 1. The converter provides high precision analog to digital conversion at low power. In operation, the converter circuit 108 is coupled to receive an analog input signal 402 on a line 404 that is coupled to a lead electrode (not shown) and to provide a corresponding digital output signal 406 on an output line 408. The analog input signal includes a biometric signal and an interferer signal. In some embodiments, the interferer signal has a larger amplitude and a lower frequency range than the biometric signal.

Figure 4:
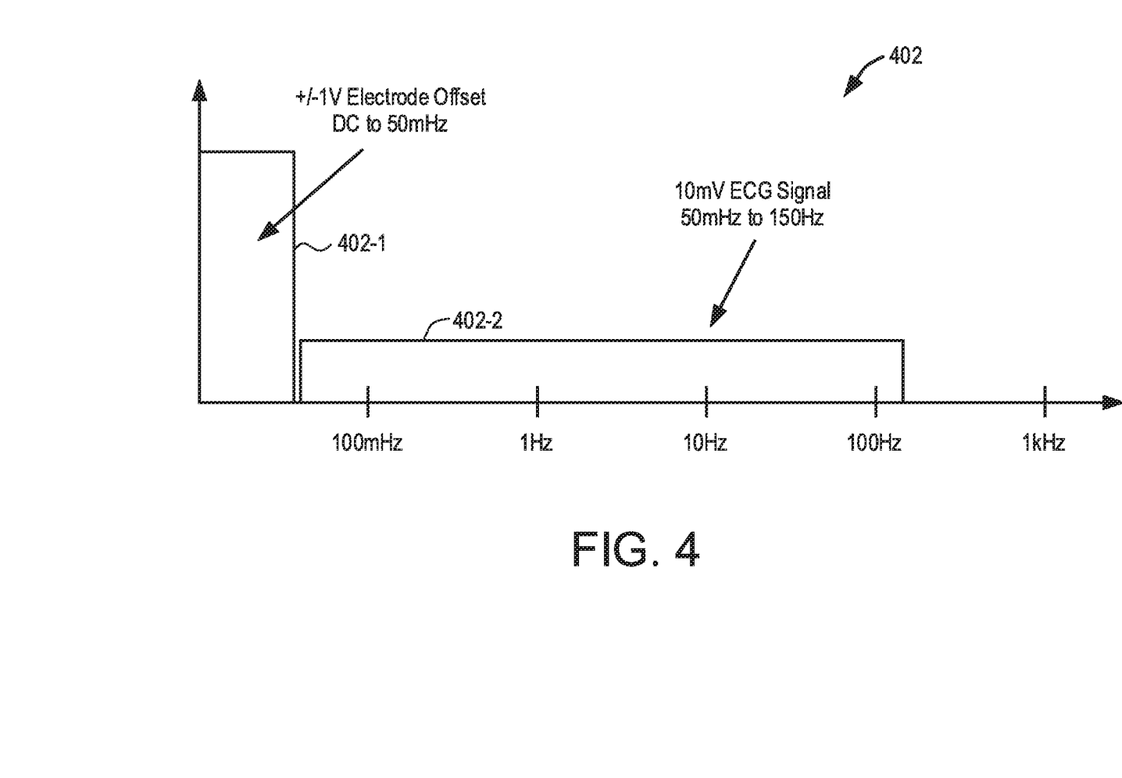
FIG. 4 is an illustrative voltage versus frequency diagram in which a y axis represents an example input signal that includes an example biometric signal and an example of a large interferer signal and an x axis represents a signal a signal frequency range.

FIG. 4 is an illustrative voltage versus frequency diagram in which a y axis represents an example input signal 402 that includes an example biometric signal 402-1 of interest and an example interferer signal. The biometric signal 402-1 includes an ECG signal and the interferer signal 402-2 includes a near-DC electrode offset interferer signal. The example ECG signal has a maximum amplitude of 10 mV with a frequency content between 50 mHz and 150 Hz. ECG electrode leads often develop an ionic potential at the electrode-skin interface that can drift slowly (DC to 50 mHz). The example near-DC offset interferer signal has a value of +/−1V from DC to 50 mHz.

Referring again to FIG. 3, in one embodiment, the converter circuit 108 removes the lower frequency analog interferer component signal 402-2 from the analog input signal 402 and amplifies the remaining analog biometric component signal 402-1 to produce an amplified version of the analog biometric component signal 410. The converter circuit 108 converts the amplified analog biometric component signal 410 to the corresponding digital output signal 406 version of the biometric signal. More particularly, the converter circuit 108 includes a sub-ranging capacitive analog front end (AFE) that includes a capacitive difference circuit 412 (indicated by dashed lines) that includes a first input capacitor C1 and a second feedback capacitor C2. The circuit 108 includes a capacitive gain amplifier 413 configured to gain the difference signal in proportion to a ratio of capacitors C3 and C1. The circuit 108 includes a sigma delta analog to digital converter (ΣΔ ADC) 415 that provides the digital output signal 406. The circuit 108 also includes a digital feedback loop 430 that includes a digital integrator circuit 416 and a digital oversampled capacitive digital to analog converter (DAC) 418.

The capacitive difference circuit 412 includes the first capacitor C1 and the second feedback capacitor C2. The capacitive difference circuit 412 is configured to couple the analog input signal 402 on line 404, via the first capacitor C1, to an input node 405 of the capacitive difference amplifier 409 The capacitive difference circuit 412 is further configured to couple an analog feedback signal 420, indicative of charge applied to the feedback capacitor C2, to the input node 405. As explained more fully below, the second feedback amplifier C2 is a component of the digital oversampled capacitive DAC 418.

The capacitive difference amplifier 409 is coupled to receive an analog difference signal 424 at node 405 that represents a difference between the analog input signal 402 and the analog feedback signal 420 in proportion to the ratio of capacitors C1 and C2 and to provide the amplified analog difference signal 410 at amplifier output node 413. The capacitive difference amplifier 409 includes an amplifier circuit 411 that amplifies the difference signal 424 in proportion to the ratio of C3 and C1. In some embodiments, the capacitive gain amplifier 411 is configured to chop the input signal, analog loop feedback signal and amplified difference signal at a frequency above the 1/f noise corner to eliminate 1/f noise of the amplifier in the band of interest of the biometric signal. The SD ADC 415 is coupled to receive the amplified analog difference signal 410 and to convert it to the digital output signal 406. The digital integrator 416 is coupled to receive the digital output signal 406 and to provide a digital integration signal 428. Coefficients of the digital integrator 416 can be programmed to adjust the bandwidth of the digital integrator which also correspondingly adjusts the bandwidth of the mixed signal feedback loop. The capacitive DAC 418 is coupled to receive the digital integration signal 410 and to convert it to the analog feedback signal 420. The integrator 416 performs an integration function to produce an integrator output signal 428 such that the loop gain of the feedback loop is maximized at low frequency. This leads the integrator output signal 428 to cancel the interferer signal at the input 404 so that the input signal of the integrator 406 on line 407 is minimized at low frequency.

The digital integrator 416 is configured to impart greater amplification to lower frequency digital signals in a frequency range of the interferer, e.g., a near-DC electrode offset signal, than to digital signals in the higher frequency range of the biometric, e.g., an ECG signal in one embodiment. As a consequence, the digital integrator 416 produces a digital integration signal 428 on line 429 that represents an amplified digital version of the lower frequency interferer signal.

The capacitive DAC 418 converts the digital integration signal 428 to produce the analog feedback signal 420 on feedback line 422, which acts as an analog cancellation signal to cancel the interferer signal from the input signal 402. The capacitive difference circuit 412 produces the difference signal 424. The lower frequency interferer signal portion of the input signal 402 received via capacitor C1 and the feedback signal 420 received on line 422 via capacitor C2 cancel each other at node 405, to thereby produce the difference signal 424 at node 405, which includes the biometric signal of the input signal 402 with the interferer signal removed.

Removal of the larger magnitude interferer signal permits use of a capacitive difference amplifier 409 having a higher gain, which in turn, permits use of a lower power, lower bit resolution SD ADC 415, without loss of system resolution and Signal to Noise ratio (SNR) requirements. More specifically, the capacitive difference amplifier 409 can be used to provide greater amplification without becoming over-ranged, since it is used to amplify the smaller magnitude difference component signal 424 that remains after the larger magnitude interferer signal has been removed by the capacitive difference circuit 412. As a result, a lower bit resolution SD ADC 415 that consumes less power can be used without loss of accuracy of the converted digital signal 406. In operation, the difference circuit produces at node 405 a voltage signal 424 indicative of a difference between a charge in the first (input) capacitor C1 and applied to the second (analog loop feedback) capacitor C2. The use of capacitors C1, C2 to produce the difference signal 424 based upon the input signal 402 and the analog loop feedback signal 420 and the use of the ratio C3/C1 to produce an amplified version of the difference signal 410 results in high precision. In particular, integrated circuit MiM capacitors used for C1, C2 and C3 are fabricated on silicon processes that match with high precision and repeatability. Further oversampling and sigma delta techniques can be used on the Cap DAC to shape away mismatch errors to higher frequency to achieve high linearity at low frequency.

Figure 5:
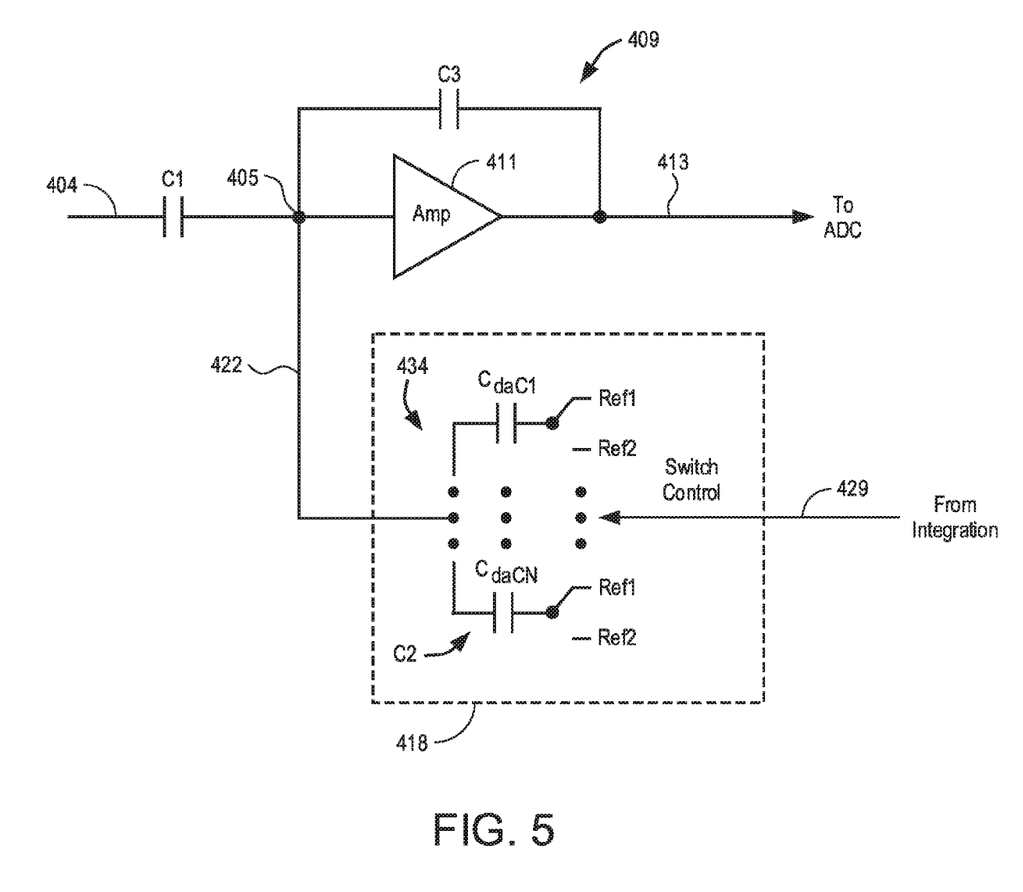
FIG. 5 is an illustrative circuit diagram showing certain components of the capacitive DAC incorporated into the capacitive gain amplifier of FIG. 4.

The second (loop feedback) capacitor C2 is an array of unit capacitors that form the oversampled capacitive SD DAC 418. FIG. 5 is an illustrative circuit diagram showing certain components of the SD DAC 418 coupled to the capacitive difference amplifier 409. The SD DAC 418 includes an array 434 of unit capacitors Cdac1 to Cdacn and switches $SW_1$ to $SW_N$ to selectively couple individual unit capacitors of the array to one of a first and second reference values. The amplifier circuit 409 is coupled to receive the input signal 402 on line 404 via an input capacitor C1 and to receive the feedback signal 420 on line 422 by selecting a combination of switches such that some of the SD DAC array unit capacitors $Cdac_1$ to $Cdac_N$ are connected to Ref1 and the rest of the SD DAC array unit capacitors $Cdac_1$ to $Cdac_N$ are connected to Ref2 in the unit capacitor array 434. The DAC unit capacitors are used to create the analog feedback signal 420 from the digital feedback signal 428 by selecting the capacitors using dynamic elements matching (DEM) techniques to shape the capacitor mismatch between the unit capacitors $Cdac_1$ to $Cdac_N$ into high pass shaped noise. This prevents capacitance mismatch from degrading linearity and SNR performance inside the frequency band of the signal of interest signal 202. The use of a capacitive feedback DAC 418 allows the use of oversampled sigma delta techniques like DEM to achieve high (e.g., 19 bit) linearity using capacitors whose inherent matching is lower (e.g., about 8 bits) linearity. The linearity performance of the SD DAC 418 directly influences the system linearity and SNR performance. Thus, use of a capacitive front end in conjunction with a sigma delta feedback loop achieves a high performance low power system.

It will be appreciated that the converter circuit 108 includes a capacitive difference amplifier 409 coupled to provide an amplified difference signal 410 to the SD ADC 415 in which the capacitive difference amplifier 409 and the SD ADC 415 are themselves coupled with a feedback circuit that acts as a sigma delta feedback loop. More specifically, the digital integrator circuit 416 performs a "sigma" (integrator) function. The capacitive difference circuit 412 performs a "delta" (difference) function. In such a sigma delta feedback loop, in some embodiments, the bandwidth of the loop can be maximized so that both the signal of interest and the interference signal are present in the feedback DAC 418. The input signal 402 and the feedback signal 420 cancel so that the amplifier 423 processes a difference signal that includes only the quantization noise of the sigma delta feedback loop. This permits increasing the gain of the amplifier further and in conjunction with a lower resolution lower power sigma delta ADC further reducing system power. This further permits operation of the difference amplifier from a lower power supply further reducing power consumption of the system.

Figure 6:
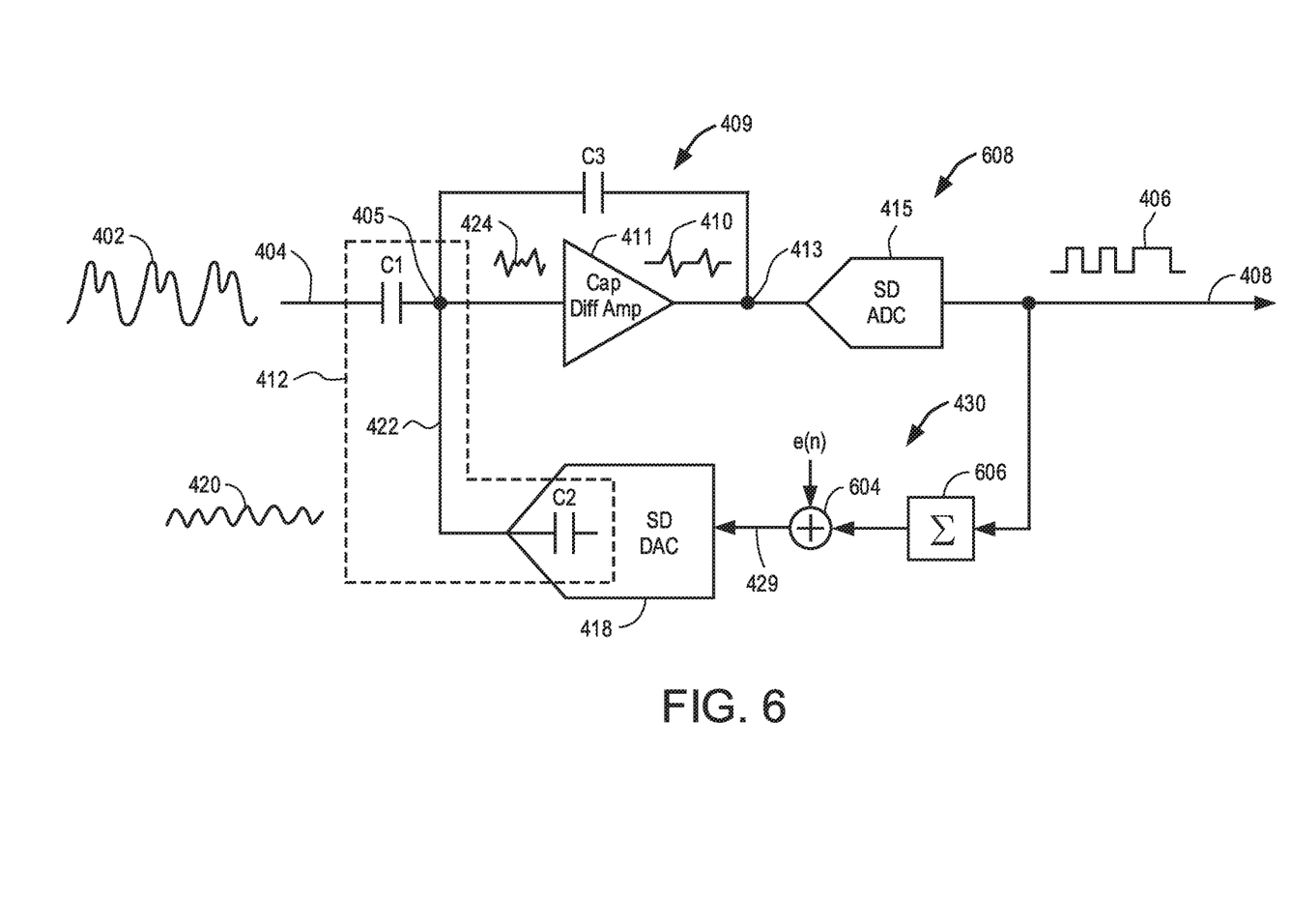
FIG. 6 is an illustrative circuit diagram representing a second converter circuit that includes a quantizer in accordance with some embodiments.

FIG. 6 is an illustrative circuit diagram representing a second converter circuit that includes a quantizer 604 in accordance with some embodiments. A digital summation circuit 602 sums digital input signals at a specific ratio that it receives as input realizing the integration function 416. It will be appreciated that an internal coefficient value of the summation circuit 606 can be adjusted to configure a bandwidth of the summation circuit 606 and to thereby configure the bandwidth of the feedback loop 430. The digital summation circuit 606 is followed by the quantizer circuit 604 to reduce the number of quantization levels of the DAC 418. Implementing a high linearity, high resolution DAC using unit capacitor elements is not practical due to size and power limitations. Accordingly, in some embodiments, the quantizer circuit 604 is used to reduce the number of bits of quantization to enable the use of a lower resolution, high linearity DAC.

Figure 7:
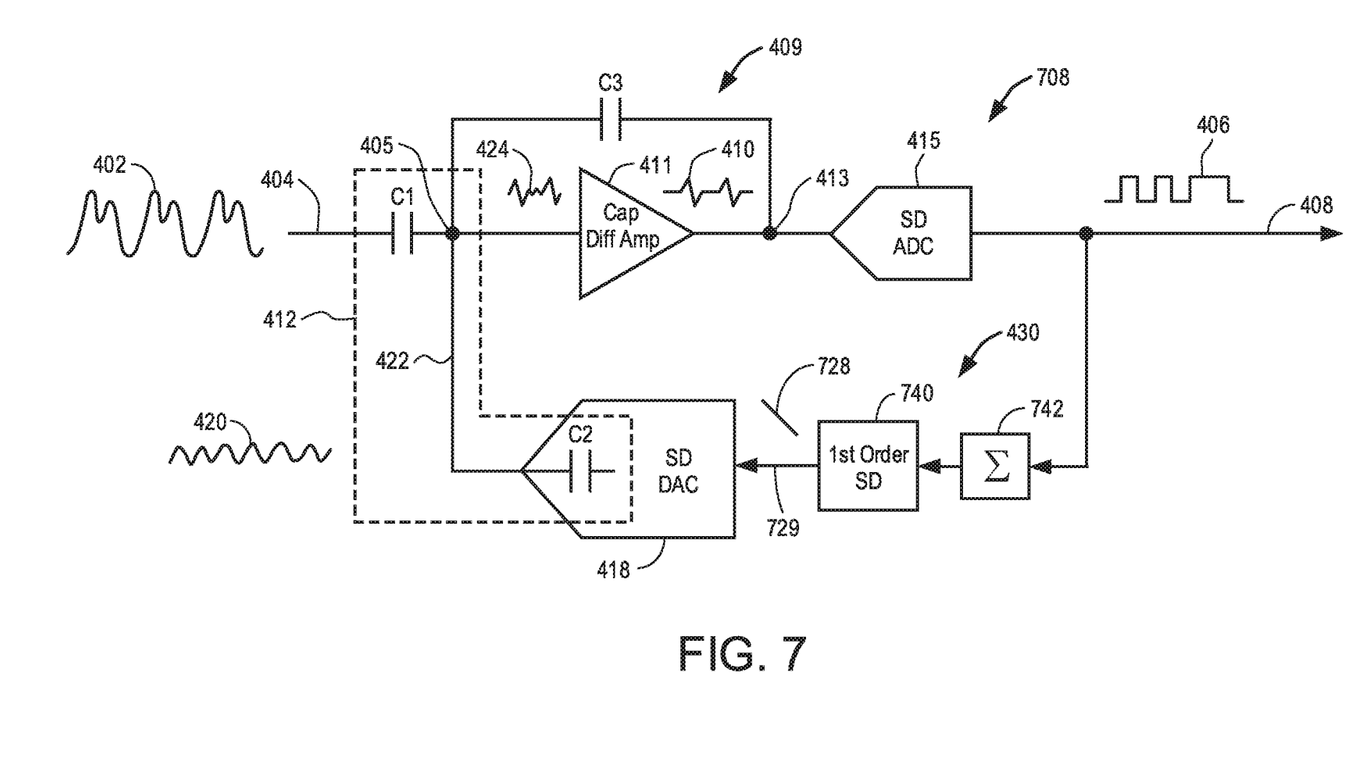
FIG. 7 is an illustrative circuit diagram representing a third converter circuit that includes a first order digital sigma delta quantizer in accordance with some embodiments.

FIG. 7 is an illustrative circuit diagram representing a third converter circuit that includes a digital first order sigma delta quantizer 740 in accordance with some embodiments. A digital summation circuit 742 receives a digital signal 406 from the SD ADC 415 and provides a digital integrator signal to the SD quantizer 740. As explained above, an internal coefficient value of the summation circuit 742 can be adjusted to configure a bandwidth of the summation circuit 742 and to thereby configure the bandwidth of the feedback loop 430. The first order SD quantizer 740 acts not only to quantize the digital integrator signal but also to shape the quantization noise away from band of interest. Incorporating the first order SD quantizer 740 in the sigma delta feedback loop provides second order quantization noise shaping up to the loop bandwidth followed by first order noise shaping. This further minimizes the quantization noise in the frequency band of interest. In in an alternative embodiment, an input of the SD DAC 729 can be used as an output of the converter 708.

The above description is presented to enable any person skilled in the art to create and use an ADC with capacitive difference circuit and a mixed signal sigma delta feedback. Various modifications to the embodiments will be readily apparent to those skilled in the art, and the generic principles defined herein may be applied to other embodiments and applications without departing from the spirit and scope of the invention. For example, a digital differentiator (not shown) can be substituted in the circuit of FIG. 3 in place of the integrator 416. Such digital differentiator amplifies higher frequency signals, and therefore, can be used to produce a feedback signal on line 422 that cancels a higher frequency interferer. Moreover, for example, although the above-described embodiments disclose converters configured as single-ended circuits, the same principles apply to a converter configured as a differential circuit.

In the preceding description, numerous details are set forth for the purpose of explanation. However, one of ordinary skill in the art will realize that the invention might be practiced without the use of these specific details. In other instances, well-known processes are shown in block diagram form in order not to obscure the description of the invention with unnecessary detail. Identical reference numerals may be used to represent different views of the same or similar item in different drawings. Thus, the foregoing description and drawings of embodiments in accordance with the present invention are merely illustrative of the principles of the invention. Therefore, it will be understood that various modifications can be made to the embodiments by those skilled in the art without departing from the spirit and scope of the invention, which is defined in the appended claims.

The invention claimed is:

1. A low power analog-to-digital converter system comprising:
   a capacitive difference circuit, coupled to receive an analog input signal and to receive an analog loop feedback signal, and to output an analog difference signal representing a difference between the analog input signal and the analog loop feedback signal;
   a capacitive difference amplifier circuit configured to amplify the analog difference signal in proportion to a ratio of a first capacitance of the capacitive difference circuit and a second capacitance of the capacitive difference circuit to provide an amplified analog difference signal;
   a sigma-delta analog-to-digital converter (SD-ADC) coupled to produce a digital output signal based upon the amplified analog difference signal;
   a digital integrator circuit, coupled to receive the digital output signal and to provide a digital integration signal; and
   a capacitive digital-to-analog converter (DAC) coupled to produce the analog loop feedback signal based upon the digital output signal.

2. The system of claim 1,
   wherein the analog input signal includes a biometric signal portion within a first frequency range and includes an interferer signal portion within a second frequency range; and
   wherein the analog loop feedback signal includes a signal portion within the second frequency range.

3. The system of claim 1,
   wherein the analog input signal includes a biometric signal portion within a first higher frequency range and includes an interferer signal portion within a second lower frequency range; and
   wherein the digital integrator is configured to pass a portion of the digital output signal in the second lower frequency range and to block a portion of the digital output signal in the first higher frequency range.

4. The system of claim 1,
   wherein the analog input signal includes an ECG signal portion within a higher first frequency range and includes an interferer signal portion within a lower second frequency range; and
   wherein the analog loop feedback signal includes a signal portion within the lower second frequency range.

5. The system of claim 1,
   wherein the analog input signal includes a biometric signal portion within a first frequency range and includes an interferer signal portion within a second frequency range; and
   wherein the analog loop feedback signal includes a signal portion within the second frequency range.

6. The system of claim 5,
   wherein the digital integrator is configured to pass a portion of the digital output signal in the second frequency range and to block a portion of the digital output signal in the first frequency range.

7. The system of claim 5,
   wherein the digital integrator is configured to pass a digital output signal in both the first and second frequency range.

8. The system of claim 1,
   wherein the analog input signal includes an ECG signal portion within a frequency range of approximately 50 mHz to 150 Hz and has a maximum amplitude of about +/−10 mV and includes an interferer signal portion within a frequency range of approximately DC to 50 mhz and has a maximum amplitude larger than +/−1V; and
   wherein the digital integrator amplifies a component of the digital output signal in the approximately DC to 50 mHz frequency range to an amplitude level of the component of the interferer signal portion.

9. The system of claim 1,
   wherein the digital integrator includes a summation circuit; and
   wherein a bandwidth of the summation circuit can be changed by changing a co-efficient of the summation circuit to change the bandwidth of the feedback loop.

10. The system of claim 1,
    wherein the digital integrator includes a summation circuit; and further followed by:
    a quantizer circuit coupled to quantize a digital integrator signal and to provide the quantized digital integrator signal to the capacitive DAC.

11. The system of claim 1,
    wherein the digital integrator includes a summation circuit; and further followed by:
    a digital sigma delta quantizer coupled to quantize a digital integrator signal and to provide the quantized digital integrator signal to the capacitive DAC.

12. The system of claim 1,
    wherein the capacitive DAC includes circuitry configured to use oversampling to minimize an effect of a capacitor mismatch.

13. The system of claim 1,
    wherein the capacitive DAC includes circuitry configured to use a dynamic elements matching technique to shape an effect of a capacitor mismatch.

14. The system of claim 1,
    wherein the capacitive difference circuit includes first capacitor coupled to receive charge proportional to the input signal and a second capacitor coupled to receive charge proportional to the loop feedback signal.

15. A low power analog-to-digital converter system comprising:
    a capacitive difference circuit that includes a first capacitor coupled to receive charge proportional to an input signal and a second capacitor coupled to receive charge proportional to an analog loop feedback signal and to provide an analog difference signal proportional to a ratio of capacitances of the first capacitor and the second capacitor;
    a capacitive difference amplifier circuit that includes an amplifier circuit and a third capacitor configured to amplify the analog difference signal in proportion to a ratio of capacitances of the third capacitor and the first capacitor and to provide an amplified version of the analog difference signal;
    a sigma-delta analog-to-digital converter (SD-ADC) coupled to produce a digital output signal based upon the amplified analog difference signal;
    a digital integrator circuit, coupled to receive the digital output signal and to provide a digital integration signal; and
    a capacitive digital-to-analog converter (DAC) coupled to produce the analog loop feedback signal based upon the digital integration signal.

16. The system of claim 15, wherein the capacitive difference amplifier is configured to chop the input signal, the analog loop feedback signal, and the amplified analog difference signal to eliminate 1/f noise of the capacitive difference amplifier in a frequency range of interest.

17. The system of claim 15, wherein the second capacitor is a component of the capacitive DAC.

18. The system of claim 15, wherein the capacitive DAC includes an array of unit capacitors coupled in parallel to be selectively switchable between a first reference voltage and a second reference voltage to act as the second capacitor.

19. A method for converting a low power analog input signal to a digital output signal, the method comprising:
producing an analog difference signal representing a difference between the analog input signal and an analog loop feedback signal;
amplifying the analog difference signal in proportion to a ratio of a first capacitance and a second capacitance to generate an amplified analog difference signal;
producing a digital output signal, by a sigma-delta analog-to-digital converter (SD-ADC), based at least in part on the amplified analog difference signal;
integrating the digital output signal to generate a digital integration signal; and
producing the analog loop feedback signal based at least in part on the digital integration signal.

20. A low power digital-to-analog converter system, comprising:
means for producing an analog difference signal representing a difference between an analog input signal and an analog loop feedback signal;
means for amplifying the analog difference signal in proportion to a ratio of a first capacitance and a second capacitance to generate an amplified analog difference signal;
means for producing a digital output signal based at least in part on the amplified analog difference signal, the means for producing the digital output signal comprising a sigma-delta analog-to-digital converter (SD-ADC);
means for integrating the digital output signal to generate a digital integration signal; and
means for producing the analog loop feedback signal based at least in part on the digital integration signal.

* * * * *